(12) United States Patent
Therien

(10) Patent No.: US 6,382,762 B1
(45) Date of Patent: May 7, 2002

(54) PELTIER HUMIDITY DETERMINATION SYSTEM FOR INKJET PRINTING

(75) Inventor: Patrick J. Therien, Battle Ground, WA (US)

(73) Assignee: Hewlett-Packard Company, Palo Alto, CA (US)

( * ) Notice: Subject to any disclaimer, the term of this patent is extended or adjusted under 35 U.S.C. 154(b) by 0 days.

(21) Appl. No.: 09/845,404

(22) Filed: Apr. 30, 2001

(51) Int. Cl.[7] .......................... B41J 29/393; G01N 7/00; G01S 3/02
(52) U.S. Cl. ...................... 347/19; 73/29.01; 324/76.14
(58) Field of Search ............................... 347/19, 14, 23, 347/10, 11, 12; 73/29.01, 29.05, 29.03; 374/18, 19, 20, 44, 45; 324/76.14

(56) References Cited

U.S. PATENT DOCUMENTS

| | | |
|---|---|---|
| 5,387,976 A | 2/1995 | Lesniak |
| 5,508,826 A | 4/1996 | Lloyd et al. |
| 5,612,902 A | 3/1997 | Stokes |
| 5,731,823 A | 3/1998 | Miller et al. |
| 5,760,913 A | 6/1998 | Falk |
| 5,818,960 A | 10/1998 | Gregory, Jr. et al. |
| 5,828,781 A | 10/1998 | Nakano |
| 5,877,787 A | 3/1999 | Edge |
| 6,027,201 A | 2/2000 | Edge |
| 6,030,066 A | 2/2000 | Li et al. |
| 6,038,374 A | 3/2000 | Jacob et al. |
| 6,062,137 A | 5/2000 | Guo et al. |
| 6,070,022 A * | 5/2000 | Kobayashi et al. ........... 347/12 |
| 6,076,915 A | 6/2000 | Gast et al. |
| 6,081,353 A | 6/2000 | Tanaka et al. |
| 6,128,022 A | 10/2000 | Dillinger |
| 6,157,469 A | 12/2000 | Mestha |
| 6,160,968 A | 12/2000 | Noda |
| 6,164,750 A | 12/2000 | Subirada et al. |
| 6,178,007 B1 | 2/2001 | Harrington |
| 6,185,004 B1 | 2/2001 | Lin et al. |

* cited by examiner

Primary Examiner—John Barlow
Assistant Examiner—Charles W. Stewart, Jr.

(57) ABSTRACT

A humidity determination system for a hardcopy device, such as an inkjet printing mechanism, determines ambient humidity so printing routines may be adjusted to provide fast, high quality output in all environments. The system includes a thermal device having a viewable surface with a temperature which changes in response to a control signal. An optical sensor observes the viewable surface to detect an optical change in the sensor, such as when the surface passes through the dew point. A controller determines humidity from an ambient temperature reading and the temperature of the viewable surface at which the optical change occurs. With this information, the controller may change operating parameters of the hardcopy device. A hard copy device having such a humidity determination system is also provided, along with methods of determining humidity and operating a hardcopy device.

56 Claims, 3 Drawing Sheets

PELTIER HUMIDITY DETERMINATION SYSTEM FOR INKJET PRINTING

The present invention relates generally to inkjet printing mechanisms, and more particularly to an optical system for determining ambient humidity where an inkjet printing mechanism is operating, so printing routines may be adjusted to provide fast, high quality output in all environments.

Inkjet printing mechanisms use pens which shoot drops of liquid colorant, referred to generally herein as "ink," onto a page. Each pen has a printhead formed with very small nozzles through which the ink drops are fired. To print an image, the printhead is propelled back and forth across the page, shooting drops of ink in a desired pattern as it moves. The particular ink ejection mechanism within the printhead may take on a variety of different forms known to those skilled in the art, such as those using piezo-electric or thermal printhead technology. For instance, two earlier thermal ink ejection mechanisms are described and shown in U.S. Pat. Nos. 5,278,584 and 4,683,481, both assigned to the present assignee, Hewlett-Packard Company. In a thermal system, a barrier layer containing ink channels and vaporization chambers is located between a nozzle orifice plate and a substrate layer. This substrate layer typically contains linear arrays of heater elements, such as resistors, which are energized to heat ink within the vaporization chambers. Upon heating, an ink droplet is ejected from a nozzle associated with the energized resistor. By selectively energizing the resistors as the printhead moves across the page, the ink is expelled in a pattern on the print media to form a desired image (e.g., picture, chart or text).

To clean and protect the printhead, typically a "service station" mechanism is mounted within the printer chassis so the printhead can be moved over the station for maintenance. For storage, or during non-printing periods, the service stations usually include a capping system which hermetically seals the printhead nozzles from contaminants and drying. To facilitate priming, some printers have priming caps that are connected to a pumping unit to draw a vacuum on the printhead. During operation, partial occlusions or clogs in the printhead are periodically cleared by firing a number of drops of ink through each of the nozzles in a clearing or purging process known as "spitting." The waste ink is collected at a spitting reservoir portion of the service station, known as a "spittoon." After spitting, uncapping, or occasionally during printing, most service stations have a flexible wiper, or a more rigid spring-loaded wiper, that wipes the printhead surface to remove ink residue, as well as any paper dust or other debris that has collected on the printhead.

To improve the clarity and contrast of the printed image, recent research has focused on improving the ink itself. To provide quicker, more waterfast printing with darker blacks and more vivid colors, pigment based inks have been developed. These pigment based inks have a higher solids content than the earlier dye-based inks, which results in a higher optical density for the new inks. Both types of ink dry quickly, which allows inkjet printing mechanisms to use plain paper.

Various environmental factors affect inkjet printing routines, servicing routines, and other aspects of printer performance. Unfortunately in the past, there has been no way to economically provide an environmental factor input to a printer controller to allow the controller to modify these printing, servicing and other routines to provide optimum performance in light of the current environmental conditions. One environmental factor, temperature, may currently be monitored using temperature sensing resistors within the inkjet printheads; however, more important to printer performance than temperature is the environmental factor of humidity. Unfortunately, the currently available humidity sensors are far too expensive for the home and small business inkjet printing markets, with manufacturer's material costs for capacitive sensors ranging several dollars per sensor not including the cost of their support electronics, while voltage output humidity sensors currently cost about ten dollars each. Moreover, the currently available capacitive humidity sensors are inaccurate, so their inaccuracy coupled with their high cost renders their use unjustifiable in the home and small business inkjet printing market.

If humidity could be both economically and accurately measured for communication to a printer controller, a variety of performance enhancements could be made based upon knowledge of the ambient humidity. For example, presently to provide optimum performance in varying environmental conditions, inkjet printing, servicing, and other routines are based on a "worst case scenario" assumption of the environmental conditions, here meaning a high humidity environment for printing and a low humidity environment for printhead servicing, as well as for vapor transfer calculations which account for ink evaporation from the pens. The terms "dry" and "humid" are used herein to assist the reader in understanding which end of the scale refers to which condition. For instance, a "dry" condition normally is associated with a desert environment, whereas a "humid" condition is normally associated with a tropical environment, although it is apparent that during a cloud burst a desert may become a very humid environment for a short period of time.

In high humidity conditions, the media may already be moist and partially saturated before ever being loaded into a printer, and high humidity increases the drying time of aqueous-based inks. These high humidity conditions may lead to increased cockle of the media, a term referring to the swelling of the paper fibers when saturated with ink, causing a buckling which in extreme conditions may cause the media to buckle so high that the printhead crashes into the media, smearing the printed image and possibly damaging the printhead. Thus, a high humidity assumption increases the dry time delay for the media over that required in normal or low humidity conditions, which slows media throughput while a printer waits for one sheet to dry before depositing the next sheet on top of the previously printed sheet in the output tray. Furthermore, the low humidity assumptions for servicing increase the duration of servicing routines, which further slows media throughput.

Low humidity conditions contribute to hue shift problems, where various components of the ink evaporate over time, for instance by leaking at the printhead/cap sealing interface. In "off axis" printing systems, where the printheads carry only a small supply of ink across the printzone and are replenished with ink delivered from a stationary main ink reservoir through flexible tubing, some of the ink volatiles leach through the tubing walls to atmosphere. Any loss of one ink component changes the ink composition, resulting in changes in ink performance, often manifested as a hue shift in the resulting image. For instance, with fewer volatiles, the resulting ink dispensed by the printhead has a higher concentration of dyes or colorants, yielding a darker image than originally intended. To compensate for these ink composition changes, ambient humidity information may be used for vapor transfer rate calculations to allow for hue adjustment based on calculated dye load changes over time within the inkjet cartridges.

As another example of the impact of this high humidity assumption on printer performance, when performing duplex printing one typical duplexer unit typically holds a sheet after printing the first side for nearly seven seconds before reversing the sheet and beginning printing on the opposite surface. In low humidity conditions, such as in a desert setting, holding a sheet of paper for seven seconds as one would in a humid region unnecessarily delays duplex printing. These same delays are incurred to avoid cockle problems when printing single sided sheets. For pen servicing, it would be desirable to know the ambient humidity so the type of servicing routine performed on the printheads following uncapping and before a print job may be optimized. Additionally, by knowing a humidity history of the printer, vapor transfer rate calculations may be made to determine the amount of ink lost due to evaporation, which then may be used in conjunction with drop counting or other measures to predict when an inkjet cartridge is nearing an empty condition, allowing an operator to be warned before the cartridge runs dry.

Clearly, a variety of different printing, servicing and other performance operations may be adjusted and optimized if only the ambient humidity were input to the printing mechanism. Thus, one goal herein is to provide an ambient humidity input to an inkjet printing mechanism, which may use this input to optimize printer performance to provide fast high quality hard copy outputs.

DRAWING FIGURES

DETAILED DESCRIPTION

Figure 1:
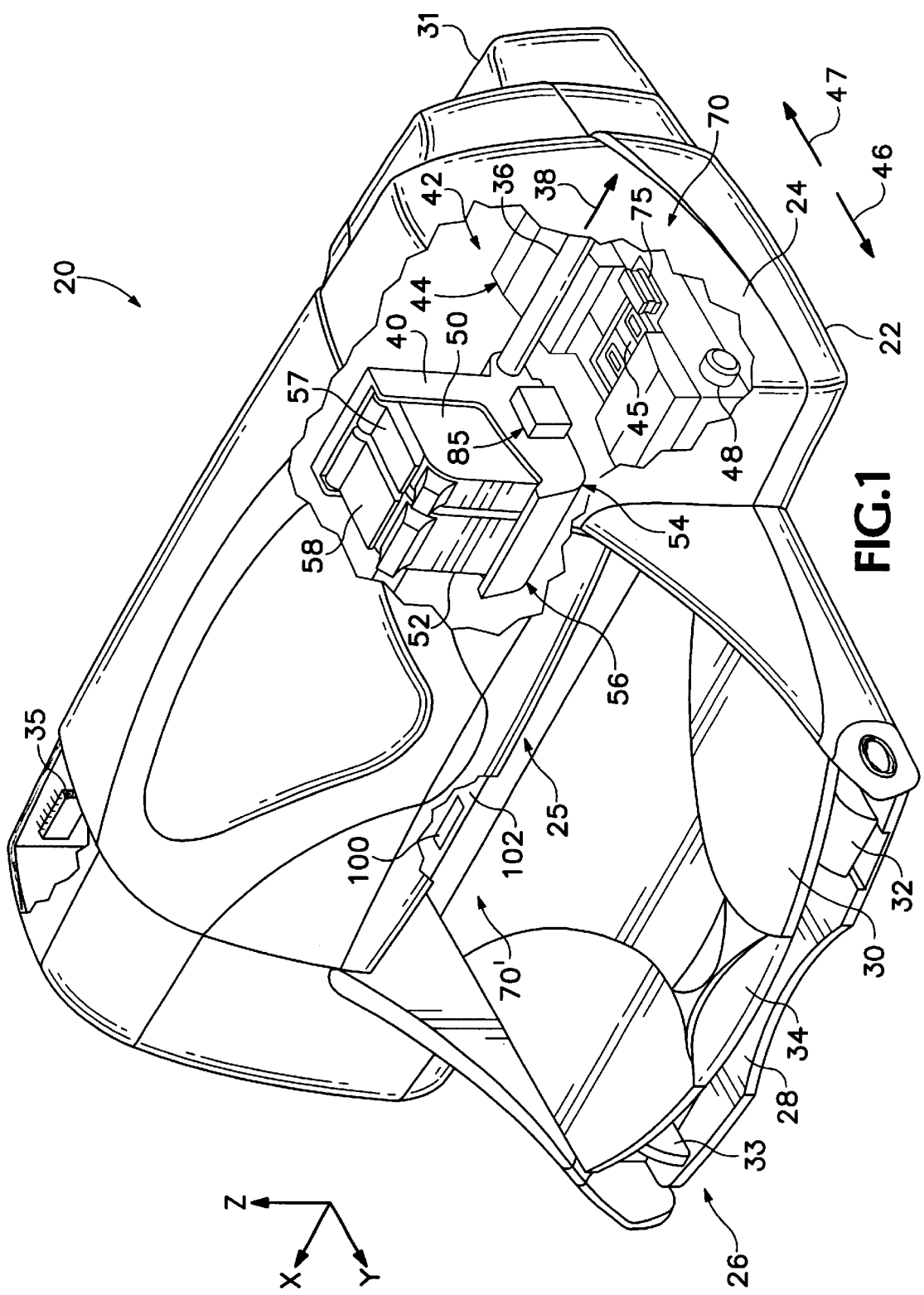
FIG. 1 is a fragmented, partially schematic, perspective view of one form of an inkjet printing mechanism including a peltier optical humidity sensing system for determining ambient humidity which affects inkjet printing.

FIG. 1 illustrates an embodiment of an inkjet printing mechanism, here shown as an inkjet printer 20, constructed in accordance with the present invention, which may be used for printing for business reports, correspondence, desktop publishing, and the like, in an industrial, office, home or other environment. A variety of inkjet printing mechanisms are commercially available. For instance, some of the printing mechanisms that may embody the present invention include plotters, portable printing units, copiers, cameras, video printers, and facsimile machines, to name a few. For convenience the concepts of the present invention are illustrated in the environment of an inkjet printer 20.

While it is apparent that the printer components may vary from model to model, the typical inkjet printer 20 includes a chassis 22 surrounded by a housing or casing enclosure 24, typically of a plastic material. Sheets of print media are fed through a printzone 25 by a print media handling system 26, constructed in accordance with the present invention. The print media may be any type of suitable sheet material, such as paper, card-stock, transparencies, fabric, mylar, and the like, but for convenience, the illustrated embodiment is described using paper as the print medium. The print media handling system 26 has a feed tray 28 for storing sheets of paper before printing. A series of conventional motor-driven paper drive rollers (not shown) may be used to move the print media from tray 28 into the printzone 25 for printing. After printing, the sheet then lands on output tray portion 30.

Alternatively, the sheet may be directed to pass through a duplexing mechanism, such as a modular duplexing mechanism 31, which turns the sheet over for printing on the opposite surface from the surface first printed upon. One suitable duplexing mechanism is described in U.S. Pat. No. 6,167,231, currently assigned to the present assignee, the Hewlett-Packard Company. The media handling system 26 may include a series of adjustment mechanisms for accommodating different sizes of print media, including letter, legal, A-4, envelopes, etc., such as a sliding length and width adjustment levers 32 and 33 for the input tray, and a sliding length adjustment lever 34 for the output tray.

The printer 20 also has a printer controller, illustrated schematically as a microprocessor 35, that receives instructions from a host device, typically a computer, such as a personal computer (not shown). Indeed, many of the printer controller functions may be performed by the host computer, by the electronics on board the printer, or by interactions therebetween. As used herein, the term "printer controller 35" encompasses these functions, whether performed by the host computer, the printer, an intermediary device therebetween, or by a combined interaction of such elements. The printer controller 35 may also operate in response to user inputs provided through a key pad (not shown) located on the exterior of the casing 24. A monitor mounted on the casing 24 or coupled to the computer host may be used to display visual information to an operator, such as the printer status or a particular program being run on the host computer. Personal computers, their input devices, such as a keyboard and/or a mouse device, and monitors are all well known to those skilled in the art.

A carriage guide rod 36 is mounted to the chassis 22 to define a scanning axis 38. The guide rod 36 slideably supports a reciprocating inkjet carriage 40, which travels back and forth across the printzone 25 and into a servicing region 42. One suitable type of carriage support system is shown in U.S. Pat. No. 5,366,305, assigned to Hewlett-Packard Company, the assignee of the present invention. A conventional carriage propulsion system may be used to drive carriage 40, including a position feedback system, which communicates carriage position signals to the controller 35. For instance, a carriage drive gear and DC motor assembly may be coupled to drive an endless belt secured in a conventional manner to the pen carriage 40, with the motor operating in response to control signals received from the printer controller 35. To provide carriage positional feedback information to printer controller 35, an optical encoder reader may be mounted to carriage 40 to read an encoder strip extending along the path of carriage travel.

Housed within the servicing region 42 is a service station 44. The service station 44 includes a translationally movable pallet 45, which moves in a forward direction indicated by arrow 46, and in a rearward direction indicated by arrow 47, when driven by a motor 48 operating in response to instructions received from the controller 35. While a variety of different mechanisms may be used to couple the drive motor 48 to the pallet 45, preferably a conventional reduction gear assembly drives a pinion gear which engages a rack gear formed along the undersurface of the pallet 45, for instance as shown in U.S. Pat. Nos. 5,980,018 and 6,132,026, both currently assigned to the present assignee, the Hewlett-Packard Company.

In the printzone 25, the media sheet receives ink from an inkjet cartridge, such as a black ink cartridge 50 and/or a color ink cartridge 52. The cartridges 50 and 52 are also often called "pens" by those in the art. The illustrated color pen 52 is a tri-color pen, although in some embodiments, a set of discrete monochrome pens may be used. While the color pen 52 may contain a pigment based ink, for the purposes of illustration, pen 52 is described as containing three dye based ink colors, such as cyan, yellow and magenta. The black ink pen 50 is illustrated herein as containing a pigment based ink. It is apparent that other types of inks may also be used in pens 50, 52, such as thermoplastic, wax or paraffin based inks, as well as hybrid or composite inks having both dye and pigment characteristics.

The illustrated pens 50, 52 each include reservoirs for storing a supply of ink. The pens 50, 52 have printheads 54, 56 respectively, each of which have an orifice plate with a plurality of nozzles formed therethrough in a manner well known to those skilled in the art. The illustrated printheads 54, 56 are thermal inkjet printheads, although other types of printheads may be used, such as piezoelectric printheads. These printheads 54, 56 typically include a substrate layer having a plurality of resistors which are associated with the nozzles. Upon energizing a selected resistor, a bubble of gas is formed to eject a droplet of ink from the nozzle and onto media in the printzone 25. The printhead resistors are selectively energized in response to enabling or firing command control signals, which may be delivered by a conventional multi-conductor strip (not shown) from the controller 35 to the printhead carriage 40, and through conventional interconnects between the carriage and pens 50, 52 to the printheads 54, 56.

Preferably, the outer surface of the orifice plates of printheads 54, 56 lie in a common printhead plane. This printhead plane may be used as a reference plane for establishing a desired media-to-printhead spacing, which is one important component of print quality. Furthermore, this printhead plane may also serve as a servicing reference plane, to which the various appliances of the service station 45 may be adjusted for optimum pen servicing. Proper pen servicing not only enhances print quality, but also prolongs pen life by maintaining the health of the printheads 54 and 56. To hold the pens, 50, 52 in place securely against alignment datums formed within carriage 40, preferably the carriage 40 includes black and color pen latches 57, 58 which clamp the pens 50, 52 in place as shown in FIG. 1.

Figure 2:
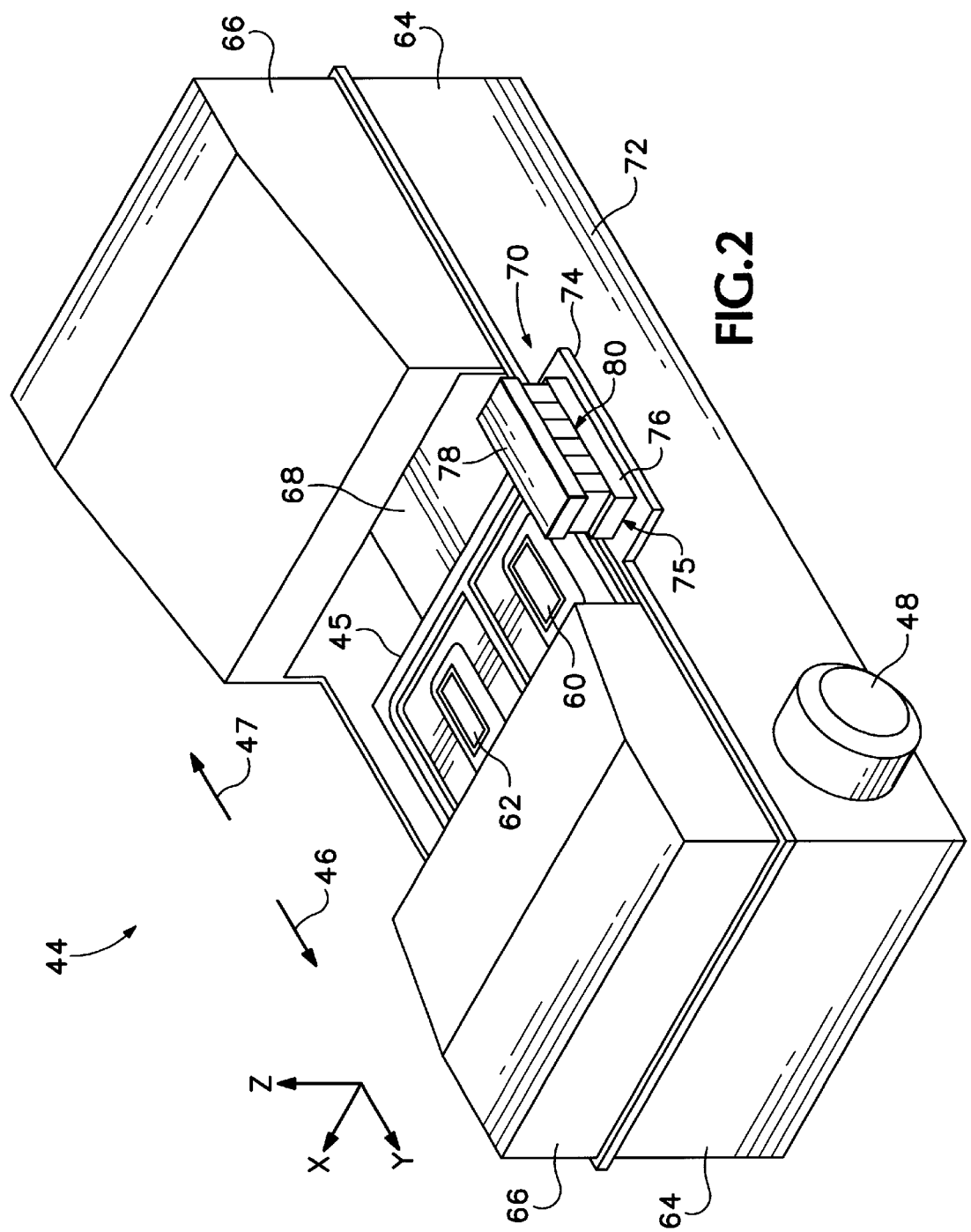
FIG. 2 is an enlarged, perspective view of one form of a service station of FIG. 1.

FIG. 2 shows one form of the service station 44, constructed in accordance with the present invention. The pallet 45 may carry a variety of different servicing members for maintaining the health of the printheads 54, 56, such as printhead wipers, primers, solvent applicators, caps and the like. These various servicing members are represented in the drawing figures as black and color caps 60, 62 for sealing the printheads 54, 56 of pens 50, 52, respectively. Preferably, the pallet 45 is housed between a lower frame portion 64, and an upper frame portion 66 of the service station 44. As mentioned above, the motor 48 drives the pallet 45 in the forward and reverse directions of arrows 46 and 47 to bring the various servicing components into contact with the printheads 54, 56. The frame lower portion 64 preferably defines a waste ink reservoir or spittoon 68, which receives ink purged from the printheads 54, 56 in a spitting routine.

The service station 44 includes an ambient humidity determination system 70 constructed in accordance with the present invention, here shown as being mounted in-part along an outboard wall 72 of the lower frame 64. As used herein, the term "inboard" refers to items facing toward the printzone 25, and the term "outboard" refers to items facing away from printzone. First an explanation of the construction of the ambient humidity determination system 70 will be given, followed by a discussion of its operation. The outboard wall 72 supports a platform 74, which projects outwardly from the wall. The peltier humidity determination system 70 includes a temperature controlling member or thermal device, shown in the illustrated embodiment as a peltier temperature controlling member or thermal device 75, which changes temperature in response to a control signal from controller 35.

The peltier thermal device 75 includes a base 76 supported by platform 74, with the base operating as a heat sink. The peltier device 75 also has a target 78, which may be of a metallic material. Sandwiched between the heat sink base 76 and the target plate 78 is a heating and cooling generator unit 80, which may be made up of alternating negatively doped semiconductor sections 82 and positively doped semiconductor sections 84. The generator unit 80 operates in response to a control signal from controller 35 to cool the target 78 or heat the target 78 in selected discreet temperature steps. Peltier heating/cooling devices are commercially available, and functionally equivalent, controllable heating and cooling devices may be substituted for the illustrated peltier device. Now the construction of the illustrated peltier thermal device 75 is understood, we can turn to a discussion of how it may be used to determine ambient humidity in system 70.

The maximum atmospheric water vapor content is a strong function of the atmospheric temperature. Indeed, one earlier way to determine ambient humidity was through the use of a "sling thermometer" which had two thermometers mounted in a metal frame attached to a small length of chain or string. One thermometer is called a "dry bulb" thermometer, and the other is called a "wet bulb" thermometer. The wet bulb thermometer has a small piece of cloth tied around it, and the cloth is wet with water just prior to taking a measurement. To measure the ambient humidity, the metal frame is twirled around in a circle using the chain or string. When the temperatures have stabilized, both the wet bulb and dry bulb temperatures are recorded, then using this data in conjunction with a chart or graph, the ambient humidity is determined. Of course today, this data may be inputted into a computer or programmed calculator to arrive at the ambient humidity, rather than referring to a chart or graph.

These same basic principles are used here in the ambient humidity determination system 70. First the peltier device receives a cooling control signal from the controller 35, and in discreet temperature steps, the target 78 is cooled. Eventually, the target 78 reaches a temperature where the moisture from the air begins to condense and collect on the exposed target surface, just as moisture collects on a cold glass of lemonade on a warm summer day. The peltier device 75 may also operate in the opposite fashion. When starting from a cooled state where the target 78 is covered with condensation, the generator unit 80 may operate in response to a heating control signal from controller 35 to gradually heat the target 78 in discreet steps until the moisture returns to the atmosphere, similar to turning on the defrosters in your car to remove frost from the windshield. The temperature at which the moisture appears on the target 78 during cooling, and the temperature at which the moisture disappears on heating are the same temperature at a given ambient humidity, with this temperature being known as a "dew point."

This accumulated moisture changes the light reflective properties of the target 78 from the dry state, with these moisture droplets scattering incoming light rays. Now if there were a way to monitor and determine at what temperature this condensation began, then one would know the equivalent of the "wet bulb" temperature. As mentioned in the Introduction section above, one or both of the inkjet printheads 54 and 56 are typically manufactured with on-board temperature sensing resistors, so the ambient temperature can be monitored using these printhead temperature sensing resistors to arrive at a "dry bulb" temperature. Thus, the problem becomes, how to monitor at what temperature the peltier target 78 begins to gather condensation.

Fortunately, some inkjet printers, such as the DeskJet® 990 model color inkjet printer produced by the Hewlett-Packard Company of Palo Alto, Calif., are equipped with an optical sensor which is used to detect ink droplets and incoming media. Such an optical sensor, or a monochromatic optical sensor as described in the Hewlett-Packard Company's U.S. Pat. No. 6,036,298, shown in FIG. 3 as an optical sensor 85, may be used as another component of the illustrated ambient humidity determination system 70. The illustrated optical sensor 85 includes a body 86, which in the illustrated embodiment is supported by an outboard side wall of the printhead carriage 40. The body 86 houses several components, including an illuminating element 88, such as a blue or violet-blue light emitting diode ("LED"). The body 86 also houses a photo sensor 90, along with optional electronics for the photo sensor, such as an amplifier 92.

Figure 3:
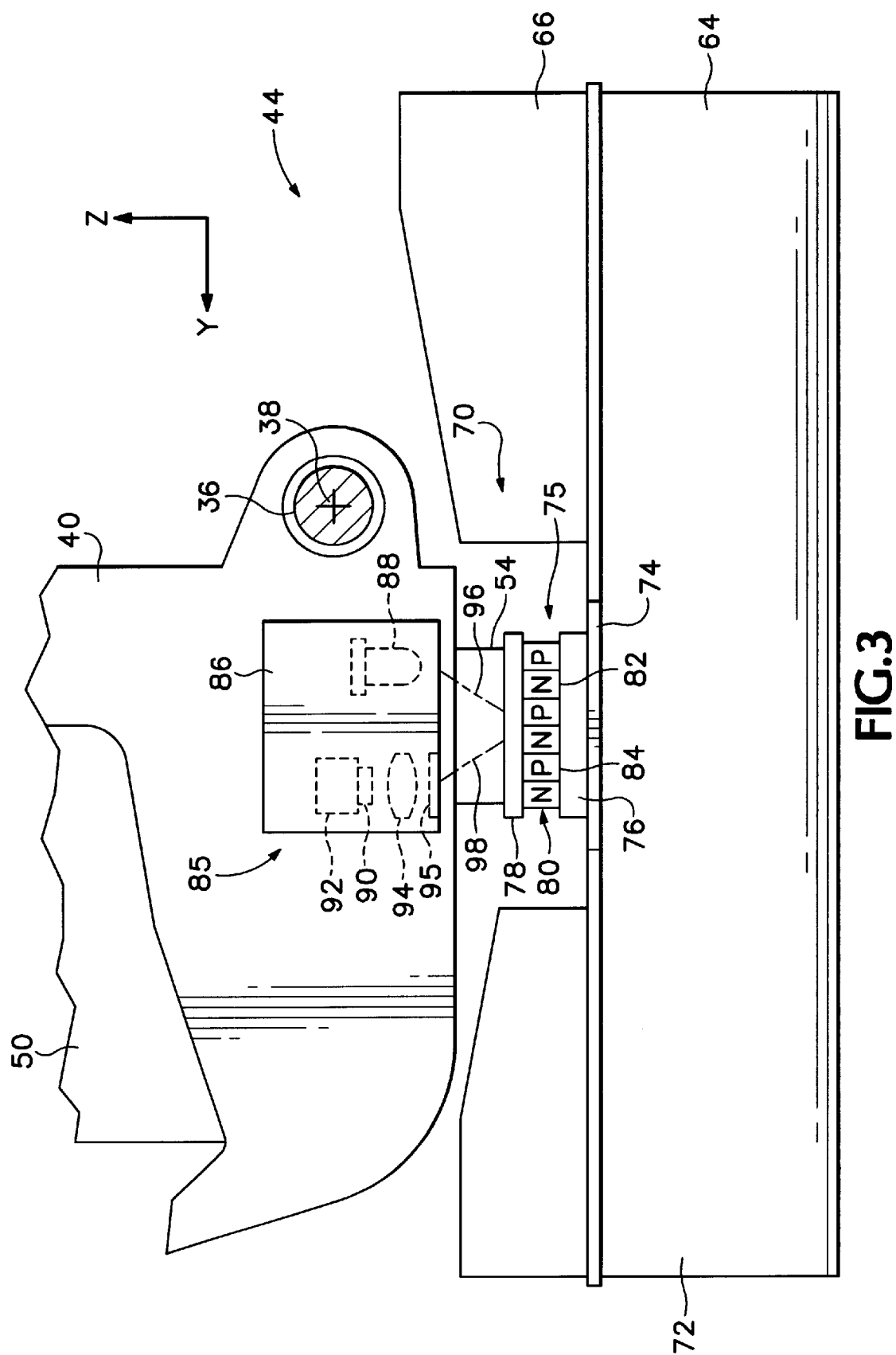
FIG. 3 is an enlarged, side elevational views of the service station of FIG. 1.

The photo sensor 90 receives light through a lens element 94, with the field of view of light passing to lens 94 being limited by a window, or F-stop 95. Optionally, an optical filter (not shown) may be placed in the F-stop window 95. The sensor body 86 may also house additional illuminating elements of different colors, along with additional photo sensors and related lens elements, etc., such as one photo sensor for monitoring diffractive reflection from the target 78, and another photo sensor for monitoring spectral reflection from the target 78. FIG. 3 shows the LED element 88 illuminating the peltier target 78 with an illuminating beam 96. The illuminating beam 96 impacts the peltier target 78, and then reflects off the target to form a reflected beam 98, which passes through any optical filter element, through the F-stop 95, and through lens 94, before being received by the photo sensor 90.

As mentioned above, the reflective properties of the target 78 change from those at a dry state to those at a wet state, with the amount of reflected light in beam 98 dropping in the wet state as the moisture droplets scatter the incoming light beam 96. In the dry state, the metallic target 78 is quite reflective, so a greater amount of light is reflected in beam 98 than in the wet state. The photo sensor 90 measures the difference in the reflected beam 98, then supplies a high signal to the controller 35 in the dry state, and a low signal to the controller 35 in the dry state. When the optical sensor 85 is monitoring the peltier target 75, the controller 35 then looks for a change from high-to-low when the generator unit 80 is cooling, and from low-to-high when the generator unit 80 is heating. Since the generator unit 80 operates in response to a control signal received from the controller 35 to increase or decrease the target temperature in discreet degree increments, the controller 35 knows at what temperature the condensation either formed or evaporated, with this temperature being the dew point, or "wet bulb" temperature. Now the controller 35 has information for both the wet bulb temperature, and the dry bulb temperature form monitoring the temperature sensing resistors on printheads 54, 56, the controller 35 may determine the ambient humidity. Actually, the ambient humidity calculation may be omitted if the controller 35 is programmed to react in various ways to these wet-bulb and dry-bulb temperature inputs, so the claims appended below this detailed description are not to be construed as being limited to requiring this optional ambient humidity calculation.

In operation, one preferred ambient humidity detection scheme, which is useful for printer 20 when operating under normal room temperature conditions, first lowers the temperature of the target 78 in a series of relatively coarse discreet steps. After reaching the dew point where condensation begins to collect on target 78, and perhaps having overshot the exact dew point because large temperature steps were being taken, the generator unit 80 then begins to raise the temperature in a series of finer or smaller temperature increase steps. The optical sensor 85 continues to monitor the target 78 during this temperature increasing routine, with the controller 35 noting a more precise temperature at which the collected condensation evaporates from the target 78. The more precise nature of the dew point temperature is a result of the smaller temperature increments being taken on the "fine adjust" heating cycle, as opposed to the larger temperature increments taken on the "coarse adjust" cooling cycle. For example, on the coarse adjust cooling cycle, temperature steps may be made in 5° or 10° increments, whereas for the fine adjust heating cycle, the temperature steps may be on the order of 1° or 5° increments. Following the heating cycle, another cooling cycle may be initiated in even finer temperature steps, followed yet by another heating cycle. The number of cooling/heating cycles employed, along with the exact temperature steps taken during each cycle, may be optimized to consume the shortest time or to provide the most accurate results.

FIG. 1 shows an optional alternative embodiment of an ambient humidity determination system 70', where a thermal device a 100, which may be constructed as described above for the thermal device 75, is mounted in the printzone 25 to a portion of the media support system, here shown as a platen 102. In other implementations, it may be desirable to support the thermal device on other components and in other locations viewable by an optical sensor, such as on the printer chassis 22 or casing 24. Furthermore, the optical sensor need not be mounted on the printhead carriage 40, but instead may be mounted at a fixed stationary location on the printer 20, as long as the optical sensor is located to monitor the thermal device target 78 for condensation accumulation and evaporation. In the illustrated embodiment, the peltier thermal device 100 is located toward the far left of the platen 102, remote from the service station 44, to avoid having the target 78 become contaminated with ink aerosol generated by printheads 54, 56 during spitting routines over the service station spittoon 68. Preferably, the peltier device 100 is mounted along the platen 102 in a position where the optical sensor 85 passes over the target 78 when slewing or reciprocating back and forth across the printzone 25 in the direction of the scanning axis 38.

Now the operation of the ambient humidity determination system 70, 70' is understood, the various ways in which the controller 35 may modify the operation of printer 20 in response to the ambient humidity information will be described. First it should be understood that printer operating systems do not need to be modified in response to all ambient humidity changes. Indeed, some inkjet printing mechanisms may be more sensitive to certain variations in humidity, while other printing mechanisms appear to be relatively immune to those same changes but sensitive to other changes. The exact operating changes, as well as the exact ambient humidity levels at which such changes occur, need to be tailored to best meet the needs of different printing mechanism designs. For instance, for one printer only under very dry conditions on the order of 10–20% relative humidity, or under very humid conditions on the order of 80–90% relative humidity, the print routines may be affected, while conditions between these extremes on the order of 30–70% relative humidity, are considered to be in a normal operating range, where print modes are unaffected by humidity. Thus, only above 70% ambient humidity, and below 30% ambient humidity does the controller of this example adjust the operating routines.

One change in operating routines of printer 20 may occur at around ambient conditions of 80% relative humidity. At this higher (80%) humidity, printing routines may be slowed to allow more time for volatiles within the inks to dry. Additionally, a time delay may be inserted between printing sheets in a multiple sheet print job, allowing a previously printed sheet to dry before the next sheet is dropped upon it in the output tray 30 to avoid smearing the earlier printed sheet. This delay or dry time may be adjusted, such as by increasing the dry time delay in high humidity conditions and decreasing the dry time delay in low humidity conditions. In an inkjet printing mechanism having auxiliary drying capability, such as in printers having internal heaters, additional heat may be applied in high humidity conditions to speed drying of the ink and reduce the drying time to a shorter interval.

As another example, under these relatively dry conditions, for instance on the order of 20% ambient humidity, print speeds may be increased because dry conditions allow the volatiles within the inks to dry more quickly. For instance, during duplex printing operations, where there is normally a seven second delay time between printing a first side of a sheet and a second side, the delay time may be decreased from a nominal seven second delay time to three or four seconds. Thus, by allowing the printer controller 35 to understand through the use of the peltier humidity determination system 70, 70' that the printer is in a humid environment, in this example above 80% humidity, print quality is increased by allowing additional dry time for the inks on multiple page print jobs. Similarly, by allowing the controller 35 to know the printer is in a relatively dry environment, here less than 20% relative humidity, throughput is increased by eliminating some of the additional dry time required during nominal conditions especially in duplex printing.

As mentioned in Introduction section above, the earlier capacitive humidity sensors are currently available at a cost of approximately several dollars each, not including the cost of their support electronics, while voltage output humidity sensors cost about ten dollars each. In contrast, the illustrated peltier device 75 costs under a dollar, which imposes little additional cost on the overall printer 20, while at the same time greatly improving performance. Moreover, if the optical sensor 85 is already installed in the printing unit for monitoring the media and/or ink droplets printed on a page, there is no additional cost associated with adding the optical sensor as the peltier target reader.

The ambient humidity determination system 70 may collect environmental data over time, storing this data within a storage portion of controller 35. This monitoring of the various environmental factors by the system 70 is advantageously accomplished without requiring the carriage 40 to move from the servicing region 42. Specifically, by obtaining a humidity history using the stationary sensor 70, the water vapor transfer rate may be calculated to accommodate for evaporation of the inks from within pens 50, 52 over time. This water vapor transfer rate, in addition to counting the number of droplets fired by each printhead 54, 56 may be used to predict the amount of ink remaining in each of the pens 50, 52. Thus, a history of the ambient humidity while the pens have been capped may be gathered by controller 35. For example, under higher humidity conditions, the printheads 54, 56 are less susceptible to clogging. Thus, under high humidity conditions fewer drops need to be expended during pre-printing spitting routines.

As mentioned in the Introduction section above, low humidity conditions also contribute to hue shift problems, where various components of the ink, such as water or volatiles, evaporate or dissipate over time, for instance by leaking at the printhead/cap sealing interface or through ink delivery tubing in off-axis printing systems. If the controller 35 has a record of the changes in the ambient humidity, and knows the rates of evaporation over time under these humidity conditions, the controller may estimate the change(s) in ink composition over the lifetime of an ink supply. Knowing these changes in the ink composition over time, the controller 35 may then compensate for these changes by conducting vapor transfer rate calculations, for instance, by printing fewer dots per unit area for an aged printhead having a higher concentration of dyes or colorants due to evaporated volatiles. Thus, the controller 35 may compensate for these ink composition changes to allow for hue adjustment based on calculated dye load changes over time within the ink supplies. Furthermore, this evaporation information may be used by the controller 35 to more accurately predict an upcoming out-of-ink condition when used in conjunction with a drop-counting or other system for anticipating when the pens 50, 52 may run dry. For instance, a simple drop-counting routine may indicate an abundant ink supply remains and fail to give an operator any warning, while in reality; the pen is nearly dry due to evaporation and a warning should be given to tell the operator to have a replacement cartridge on hand.

Additionally, use of the peltier humidity determination system 70, 70' allows the various print modes to be adjusted based on environmental conditions. As mentioned above, during duplex printing jobs throughput may be adjusted to correspond to the various changes in ambient temperature and humidity, to increase throughput and/or improve print quality over results obtained using nominal or worst case assumptions about environmental conditions. Furthermore, using the service station mounted humidity determination system 70 allows for variations in the pre-print mode servicing routines, as well as other servicing routines performed during print jobs. For example, under dry conditions the nozzles of both of the printheads 54, 56 are more subject to clogging, so to accommodate for this, pre-print spitting routines may be more vigorous than required under nominal conditions. Moreover, knowing this ambient humidity information which influences printer 20 may allow for more accurate line feed calibration, which refers to the advancing of the media through the printzone 25. Line feed calculations may be impacted by expansion and contraction of the media path encoder disk, which is used to track the movement of the media through the printzone 25. In some embodiments, the encoder disk may absorb water so in a humid environment the disk expands, adding a nominal offset to the timing of the counts as an optical sensor reads equally-spaced radial lines appearing near the disk periphery. Additionally, other media movement path components, such as drive rollers, may change shape or enlarge due to high ambient moisture conditions, impacting line feed accuracy for longer media advances which are more sensitive to runout errors in both the drive rollers and in the encoder feedback system.

What is claimed is:

1. A humidity determination system for a hardcopy device, comprising:
   a thermal device having a viewable surface with a temperature which changes in response to a control signal;
   optical sensor which observes the viewable surface to detect an optical change therein; and
   a controller which determines humidity from an ambient temperature and the temperature of the viewable surface at which said optical change occurred.

2. A humidity determination system according to claim 1 wherein said optical property of said surface comprises reflectance.

3. A humidity determination system according to claim 2 wherein said reflectance changes at the dew point.

4. A humidity determination system according to claim 2 wherein said reflectance increases during a temperature increase of said surface.

5. A humidity determination system according to claim 2 wherein said reflectance decreases during a temperature decrease of said surface.

6. A humidity determination system according to claim 2 wherein said reflectance changes as moisture accumulates on said surface.

7. A humidity determination system according to claim 6 wherein said reflectance decreases as moisture accumulates on said surface.

8. A humidity determination system according to claim 2 wherein said reflectance changes as moisture evaporates from said surface.

9. A humidity determination system according to claim 8 wherein said reflectance increases as moisture evaporates from said surface.

10. A humidity determination system according to claim 1 wherein said thermal device comprises a peltier thermal device.

11. A humidity determination system according to claim 10 wherein said control signal comprises a temperature signal generated by the controller.

12. A humidity determination system according to claim 1 wherein said ambient temperature is monitored by a component of the hardcopy device.

13. A humidity determination system according to claim 12 wherein:
   said hardcopy device comprises an inkjet printing mechanism having a printhead; and
   said component comprises a temperature sensing portion of said printhead.

14. A humidity determination system according to claim 13 wherein said thermal device comprises a peltier thermal device.

15. A method of determining humidity using a hardcopy device, comprising:
   changing the temperature of a viewable surface through an optical change;
   optically observing said surface through said optical change;
   when said optical change occurs, monitoring the ambient temperature and the temperature of the viewable surface; and
   from said monitoring, determining the humidity.

16. A method according to claim 15 wherein said optical property comprises reflectance.

17. A method according to claim 16 wherein said changing comprises decreasing the temperature of the viewable surface, and said optical change comprises decreasing the reflectance.

18. A method according to claim 16 wherein said changing comprises increasing the temperature of the viewable surface, and said optical change comprises increasing the reflectance.

19. A method according to claim 15 wherein said optical change occurs at the dew drop.

20. A method according to claim 15 wherein said changing the temperature of the viewable surface comprises controlling a peltier thermal device associated with said viewable surface.

21. A method according to claim 15 wherein said monitoring of the ambient temperature comprises monitoring said ambient temperature with a component of the hardcopy device.

22. A method according to claim 21 wherein:
   said hardcopy device comprises an inkjet printing mechanism having a printhead; and
   said monitoring of the ambient temperature comprises monitoring said ambient temperature with a temperature sensing portion of said printhead.

23. A method according to claim 15 wherein:
   said hardcopy device comprises an inkjet printing mechanism having a printhead which reciprocates across a printzone in a carriage when printing and rests in a servicing region when not printing; and
   said optically observing said surface comprises using an optical sensor mounted on said carriage.

24. A method according to claim 23 wherein said optically observing comprises observing said surface in the printzone.

25. A method according to claim 23 wherein said optically observing comprises observing said surface in the servicing region.

26. A method according to claim 25 wherein:
   said hardcopy device includes a capping mechanism in the servicing region to selectively seal the printhead; and
   said optically observing comprises observing said surface when the printhead is sealed.

27. A method according to claim 26 wherein said changing the temperature of the viewable surface comprises controlling a peltier thermal device associated with said viewable surface.

28. A method of operating a hardcopy device, comprising:
   changing the temperature of a viewable surface through an optical change;
   optically observing said surface through said optical change;
   when said optical change occurs, monitoring the ambient temperature and the temperature of the viewable surface;
   from said monitoring, determining the humidity; and
   adjusting an operating parameter of said hardcopy device in response to the determined humidity.

29. A method according to claim 28 wherein said hardcopy device comprises an inkjet printing mechanism for printing on a sheet having opposing first and second surfaces, and the method further comprises:
   printing on said first surface of the sheet;
   thereafter, reversing said sheet;
   thereafter, printing on said second surface of the sheet; and
   between said printing on the first surface and printing on the second surface, drying the sheet for a selected dry time delay;

wherein said adjusting comprises adjusting the selected dry time delay.

30. A method according to claim 29 wherein said adjusting comprises reducing the selected dry time delay under dry humidity conditions.

31. A method according to claim 30 wherein said changing the temperature of the viewable surface comprises controlling a peltier thermal device associated with said viewable surface.

32. A method according to claim 28 wherein said hardcopy device comprises an inkjet printing mechanism for printing on first and second sheets, and the method further comprises:
   printing on said first sheet;
   thereafter, drying the first sheet for a selected dry time delay; and
   thereafter, printing on said second sheet;
   wherein said adjusting comprises adjusting the selected dry time delay.

33. A method according to claim 32 wherein said adjusting comprises reducing the selected dry time delay under dry humidity conditions.

34. A method according to claim 33 wherein said changing the temperature of the viewable surface comprises controlling a peltier thermal device associated with said viewable surface.

35. A method according to claim 28 wherein said hardcopy device comprises an inkjet printing mechanism having a printhead which selectively dispenses ink, and the method further comprises:
   collecting a history of said determined humidity during a period of printhead inactivity; and
   analyzing said history;
   wherein said adjusting comprises adjusting a printhead servicing routine in response to said analyzing.

36. A method according to claim 35 wherein said servicing routine comprises purging a selected amount of ink from the printhead, and said adjusting comprises reducing the selected amount of ink purged during said servicing under high humidity conditions.

37. A method according to claim 36 wherein said changing the temperature of the viewable surface comprises controlling a peltier thermal device associated with said viewable surface.

38. A method according to claim 28 wherein said hardcopy device comprises an inkjet printing mechanism having a printhead, and the method further comprises:
   selectively dispensing ink from the printhead according to a printing routine;
   collecting a history of said humidity during printhead inactivity; and
   analyzing said history to estimate an amount of ink evaporated from said printhead during said period of inactivity.

39. A method according to claim 38 further comprising:
   compiling the amount of ink dispensed from the printhead from when the printhead was initially installed in the printing mechanism; and
   estimating the amount in ink remaining in an ink supply coupled to the printhead in response to said analyzing and said compiling.

40. A method according to claim 39 further comprising:
   predicting an upcoming out of ink condition from said estimating; and
   alerting an operator of said upcoming out of ink condition.

41. A method according to claim 38 wherein said adjusting comprises adjusting the printing routine in response to said analyzing.

42. A method according to claim 41 wherein:
   said analyzing comprises determining an amount of ink volatiles evaporated from said printhead during said period of inactivity; and
   said adjusting comprises adjusting the printing routine to compensate for said evaporated volatiles.

43. A method according to claim 42 wherein said changing the temperature of the viewable surface comprises controlling a peltier thermal device associated with said viewable surface.

44. A method according to claim 28 wherein said hardcopy device comprises an inkjet printing mechanism having a printhead, and the method further comprises:
   advancing media through a printzone of the printing mechanism; and
   selectively dispensing ink from the printhead onto the media while in the printzone;
   wherein said adjusting comprises adjusting the advancing step.

45. A method according to claim 44 wherein said changing the temperature of the viewable surface comprises controlling a peltier thermal device associated with said viewable surface.

46. A hardcopy device for interacting with media, comprising:
   an interaction head which interacts with said media when in an interaction zone;
   a media handling system which advances the media through the interaction zone;
   a thermal device having a viewable surface with a temperature which changes in response to a control signal;
   an optical sensor which observes the viewable surface to detect an optical change therein; and
   a controller which determines humidity from an ambient temperature and the temperature of the viewable surface at which said optical change occurred.

47. A hardcopy device according to claim 46 wherein said surface comprises reflectance.

48. A hardcopy device according to claim 47 wherein said reflectance changes at the dew point.

49. A hardcopy device according to claim 48 wherein said reflectance changes as moisture accumulates on said surface or evaporates from said surface.

50. A hardcopy device according to claim 46 wherein said thermal device comprises a peltier thermal device.

51. A hardcopy device according to claim 50 wherein said control signal comprises a temperature signal generated by the controller.

52. A hardcopy device according to claim 46 wherein said ambient temperature is monitored by a component of the hardcopy device.

53. A hardcopy device according to claim 52 wherein said:
   said hardcopy device comprises an inkjet printing mechanism;
   said interaction head comprises a printhead; and
   said component comprises a temperature sensing portion of said printhead.

54. A hardcopy device according to claim 46 wherein:
   the interaction head reciprocates across the interaction zone; and
   the optical sensor moves with the interaction head.

55. A hardcopy device according to claim 54 wherein the optical sensor remains stationary while observing the viewable surface.

56. A hardcopy device according to claim 46 wherein:

said hardcopy device comprises an inkjet printing mechanism for printing on a sheet;

said interaction zone comprises a printzone;

said interaction head comprises a printhead;

the hardcopy device further comprises a printhead servicing region having a capping unit for sealing the printhead during periods of inactivity; and said optical sensor observes said surface when the printhead is sealed by the capping unit.

* * * * *